US011481739B1

(12) United States Patent
McKinzie

(10) Patent No.: US 11,481,739 B1
(45) Date of Patent: Oct. 25, 2022

(54) MEDICATION DISPOSAL, TREATMENT AND RECONCILIATION KIOSK DEVICE

(71) Applicant: Deberenia McKinzie, Plantation, FL (US)

(72) Inventor: Deberenia McKinzie, Plantation, FL (US)

(*) Notice: Subject to any disclaimer, the term of this patent is extended or adjusted under 35 U.S.C. 154(b) by 322 days.

(21) Appl. No.: 16/852,320

(22) Filed: Apr. 17, 2020

Related U.S. Application Data

(60) Provisional application No. 62/835,396, filed on Apr. 17, 2019.

(51) Int. Cl.

| | |
|---|---|
| *G06Q 10/00* | (2012.01) |
| *G06Q 30/02* | (2012.01) |
| *G06K 7/10* | (2006.01) |
| *G06K 7/14* | (2006.01) |
| *G06Q 20/20* | (2012.01) |
| *A61J 1/03* | (2006.01) |
| *A61J 7/02* | (2006.01) |
| *G16H 40/67* | (2018.01) |
| *G06F 21/44* | (2013.01) |
| *G06F 3/041* | (2006.01) |
| *G01G 19/414* | (2006.01) |
| *G16H 40/20* | (2018.01) |
| *G06F 3/14* | (2006.01) |
| *G06F 3/12* | (2006.01) |

(52) U.S. Cl.
CPC ............... *G06Q 10/30* (2013.01); *A61J 1/03* (2013.01); *A61J 7/02* (2013.01); *G01G 19/414* (2013.01); *G06F 3/041* (2013.01); *G06F 21/44* (2013.01); *G06K 7/10297* (2013.01); *G06K 7/1413* (2013.01); *G06Q 20/204* (2013.01); *G06Q 20/209* (2013.01); *G06Q 30/0208* (2013.01); *G06Q 30/0215* (2013.01); *G06Q 30/0277* (2013.01); *G16H 40/20* (2018.01); *G16H 40/67* (2018.01); *A61J 2200/74* (2013.01); *A61J 2205/00* (2013.01); *A61J 2205/10* (2013.01); *G06F 3/12* (2013.01); *G06F 3/14* (2013.01)

(58) Field of Classification Search
None
See application file for complete search history.

(56) References Cited

U.S. PATENT DOCUMENTS

| | | | |
|---|---|---|---|
| 2012/0004770 A1* | 1/2012 | Ooyen | G16H 40/67 700/235 |
| 2017/0199983 A1* | 7/2017 | Cano | A61J 7/02 |

FOREIGN PATENT DOCUMENTS

| | | | | |
|---|---|---|---|---|
| WO | WO-2012000097 A1 * | 1/2012 | ......... | G06F 19/3462 |

* cited by examiner

*Primary Examiner* — Kristy A Haupt
(74) *Attorney, Agent, or Firm* — Lhota & Associates, P.A.; David P. Lhota, Esq.

(57) ABSTRACT

A medication disposal and reconciliation kiosk device and processor based system for collecting, identifying and measuring the amount of medication deposited in a collection container wherein the kiosk generates a coupon or other incentive that can be used to purchase new prescriptions, refills or other items, collects pills and liquid medications, including controlled medications such as opioids, chemically treats the collected medication with a non-toxic biodegradable solution or mixture for dissolving the medication, reports medicines collected to predetermined offices or agencies and collects the medication bottles and containers for recycling. The kiosk device includes a barcode reader, keyboard, pill counter, pill identifier, liquid medication collection bin, scale for weighing medication, biodegradable safe liquid for dissolving medication collected, receipt printout, and wireless electronic transmission circuitry or devices.

20 Claims, 9 Drawing Sheets

MEDICATION DISPOSAL, TREATMENT AND RECONCILIATION KIOSK DEVICE

CROSS-REFERENCE TO RELATED APPLICATION

This application claims the benefit of provisional patent application Ser. No. 62/835,396 filed Apr. 17, 2020.

STATEMENT REGARDING FEDERALLY SPONSORED RESEARCH OR DEVELOPMENT

N/A

FIELD OF THE INVENTION

The present invention relates to a medication disposal and reconciliation kiosk device, and more particularly, to a safe, convenient, year-round automated drug collection, disposal and medication reconciliation system that can combat the opioid crisis, decrease the availability of drugs in homes that are often used for intentional drug overdoses, prevent accidental drug poisonings in young children and the elderly, improve the medication reconciliation process performed by healthcare providers, improve medication compliance by patients, thus decrease overall healthcare cost, capture and provide an extraordinary amount of HIPAA compliant data, generate revenue for pharmacies, nursing homes, etc., prevent the evolution of drug-resistant bacteria, and establish partnerships between hospital and community pharmacies and community entities, by providing a financial incentive to get individuals to dispose of unused OTC and prescription medications like opioids and other controlled and therapeutic medications.

BACKGROUND OF THE INVENTION

There exists a serious problem today with expired and unused medication that is either discarded recklessly, shared among friends and family, used after they expire, or sold or distributed illegally in the underground market or on the streets to third parties, addicts and/or children. Most people hold onto their unused medication long after the medication expiration date because they either forget they have them or do not know how or where to discard them. And when they do dispose of them, they often cavalierly throw them in the trash, flush them down the toilet or wash them down the drain. Medication that is flushed down the toilet or put down the drain eventually end up in local water tables, canals, oceans and other bodies of water exposing fish, turtles, plants and other marine life to toxic water. For people who innocently take expired medication or medication they get from family or friends, they are at increased risk of having an adverse drug event which could lead to an ER or hospital admission or unknowingly, will facilitate or contribute to the development of drug-resistant bacteria. People are often unaware that drug-resistant bacteria can develop when an infection is partially treated as a result of an individual taking a few leftover antibiotics from a previous illness they had or by taking an antibiotic for an infection that either did not require antibiotics or required a different antibiotic or medication and a longer course of treatment.

The improper and illegal handling, disposal and distribution of medication is so pervasive today that it is considered an epidemic, an "opioid crisis." The opioid crisis is killing or creating addicts out of thousands of people every day. Also, according to the CDC, "unintentional death from prescription medication overdose has recently surpassed deaths from motor vehicle crashes in the US" and according to the NSC, "is the leading cause of poisoning deaths far surpassing incidents involving chemicals, gases or other substances," According to SafeKids and other sources, "medications are the leading cause of child poisoning causing more than 10,000 children under the age of 18 to end up in emergency rooms every year for self-administering and overdosing on OTC medicines." Sadly however, there is no way to account for all the medication that is discarded or redistributed. "It has been estimated that in 2019, 4.25 billion retail prescriptions would be filled throughout the United States, 4.31 billion in 2020 and 4.38 billion in 2021 and one estimate of unused medicines in the U.S. sets the number at 3%-7% of drugs dispensed, thus loading to America's other drug problem, the nearly $2 Billion in prescription drugs wasted every year. And unfortunately, there are no effective or reliable devices available for healthcare providers to use that allows them to safely, securely, conveniently and responsibly collect, reconcile and dispose of medications they have prescribed for their patients and later advised them to stop taking for various reasons. Such medications often include antibiotics and opioids which often once discontinued, end up in the patient's pantry or medicine cabinet. If there existed a medication disposal and reconciliation device that allowed for safe collecting, disposing, identifying, measuring or counting, and rendering the disposed medication unusable, it would be well received, especially if it offered financial incentives for its use. Unfortunately, there are no such devices, systems or methods known.

There are a variety of medication waste disposal and data collection systems known in the art, but they fail to adequately address and resolve the aforementioned issues. For instance, U.S. Pat. No. 8,979,724, U.S. Publication No. 2018/0185687 and U.S. Publication No. 2015/0352389 disclose general medication disposal systems that include devices having a sealable container dimensioned to accommodate a pharmaceutical composition; and an amount of an inactivating substance, e.g., granulated or pelletized activated carbon, present inside of the sealable container. U.S. Pat. No. 8,606,596 discloses a medication waste and data collection system for use in tracking medication containers, related medication preparation and transfer procedures, medication administration and medication waste disposal. U.S. Pat. No. 8,535,711 discloses a medication disposal system for reducing the environmental release of unused and expired medications by the provision of a system and method for combining the unused or expired medication with an amount of activated carbon as part of a disposal procedure. U.S. Publication No. 2018/0001357 discloses a composition to aid in the sequestration and/or disposal of unused human or animal pharmaceutical drug or medication. U.S. Publication No. 2017/0203138 discloses an apparatus for disposal of liquid medications that includes activated carbon to capture the active ingredients in the liquid medication before disposal. Moreover, U.S. Publication No. 2015/0231673 discloses a system for safely neutralizing medication and venting gases produced by the neutralization process and includes a container holding a quantity of disposal formula, scaled with a bottle liner, a closure with a pressure relief aperture, and an amount of hardener that may be added to the disposal formula.

While a variety of medication waste disposal and data collection systems, such as the aforementioned, are known in the industry for nurses in hospitals and surgical centers and for pharmacists to use, there are no such systems available for collecting, disposing, identifying, measuring or counting, dissolving or diluting and safely disposing of pills and liquid medications while providing a financial incentive for disposal that is available for the general public and healthcare providers, where the need is great. According to the Joint Commission, the reconciliation of drugs is the method of matching a patient's prescription orders with all the drugs the patient has taken. This reconciliation is performed to prevent medication mistakes like omissions, duplications, dosing mistakes or drug interactions. Preventing harm from drugs or adverse drug events (ADEs) remains a top priority of the healthcare industry when it comes to patient safety. Adverse drug events (ADEs) account for 4.7 percent of admissions to US hospitals, and ADEs-related hospital costs are $3.8 million/hospital per annum. Implementing reconciliation of medication at all transitions in care, admission, transfer, discharge and in all ambulatory settings is therefore an effective strategy for reducing ADEs and thus, healthcare cost. Accordingly, a medication reconciliation and disposal kiosk system is needed because it will allow healthcare providers to complete and document medication reconciliation in a patient's electronic health record (EHR) during each visit, thus decreasing the incidence of ER and hospital admissions due to ADEs (medication errors, adverse drug-drug interactions, etc.), and will keep healthcare providers from sending discontinued medications back home with patients where they can end up in the hands of family members, be ingested by children leading to accidental poisoning or overdose, or in the hands of teenagers who sham them with their friends for fun. According to the DEA, after reviewing the 2017 National Survey on Drug Use and Health, six million Americans misused controlled prescription drugs, and most of the drugs misused, were obtained from the medicine cabinet of family and friends. And according to the Center for Advancing Health reports, 14%~28% of U.S. adolescents registered selling, loaning, or giving away their medicine. The instant invention addresses this need.

Existing medication disposal kiosks presently available to the public are bins that do not immediately render the disposed pills unusable, do not provide financial incentives that could help individuals pay for medications or other necessities, do not provide usable data such as the names and number of medications disposed, do not provide the number of opioids and other control substances being disposed as we continue to fight the opioid crisis, that are not available for healthcare providers as a tool for medication reconciliation, and do not provide a way to collect and recycle pill bottles as an avenue to decrease plastic being dumped in our land fields. As there are no such devices or systems known that adequately address or resolve the foregoing shortcomings, there exists a need for such a device or system. It is, therefore, to the effective resolution of the aforementioned problems and shortcomings of the prior art that the present invention is directed. The instant invention addresses this unfulfilled need in the prior art by providing a medication disposal and reconciliation device having the aforementioned specifications and attributes as contemplated by the instant invention disclosed herein.

SUMMARY OF THE INVENTION

In light of the foregoing, it is an object of the present invention to provide a medication disposal and reconciliation kiosk device and system for collecting and disposing medication in a safe, secure, convenient and responsible manner while creating financial incentives for the public to safely dispose of unused or old medications wherein the kiosk collects, identifies and measures the deposited medication and then generates a coupon or other incentive that can be used to purchase new prescriptions, refills or other items. The kiosk device collects pills and liquid medications, including controlled medications such as opioids and may chemically treat the collected medication with a non-toxic biodegradable solution or mixture. The medication disposal and reconciliation kiosk may be placed in various locations, including hospitals, doctor offices, pharmacies, stores, veterinary offices, EMS vehicles, mobile health centers, assisted living facilities, health fairs or other locations where medical services or products are sold to address the problems with unused and old medications being shared or sold on the streets and provide a way to collect recalled medication. The kiosk device includes a barcode reader, keyboard, pill counter, pill identifier, scale for weighing medication, biodegradable safe liquid for dissolving medication collected, receipt printout, wireless electronic transmission circuitry or devices and a recycle bin.

In accordance with these and other objects, which will become apparent hereinafter, the instant invention will now be described with particular reference to the accompanying drawings.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
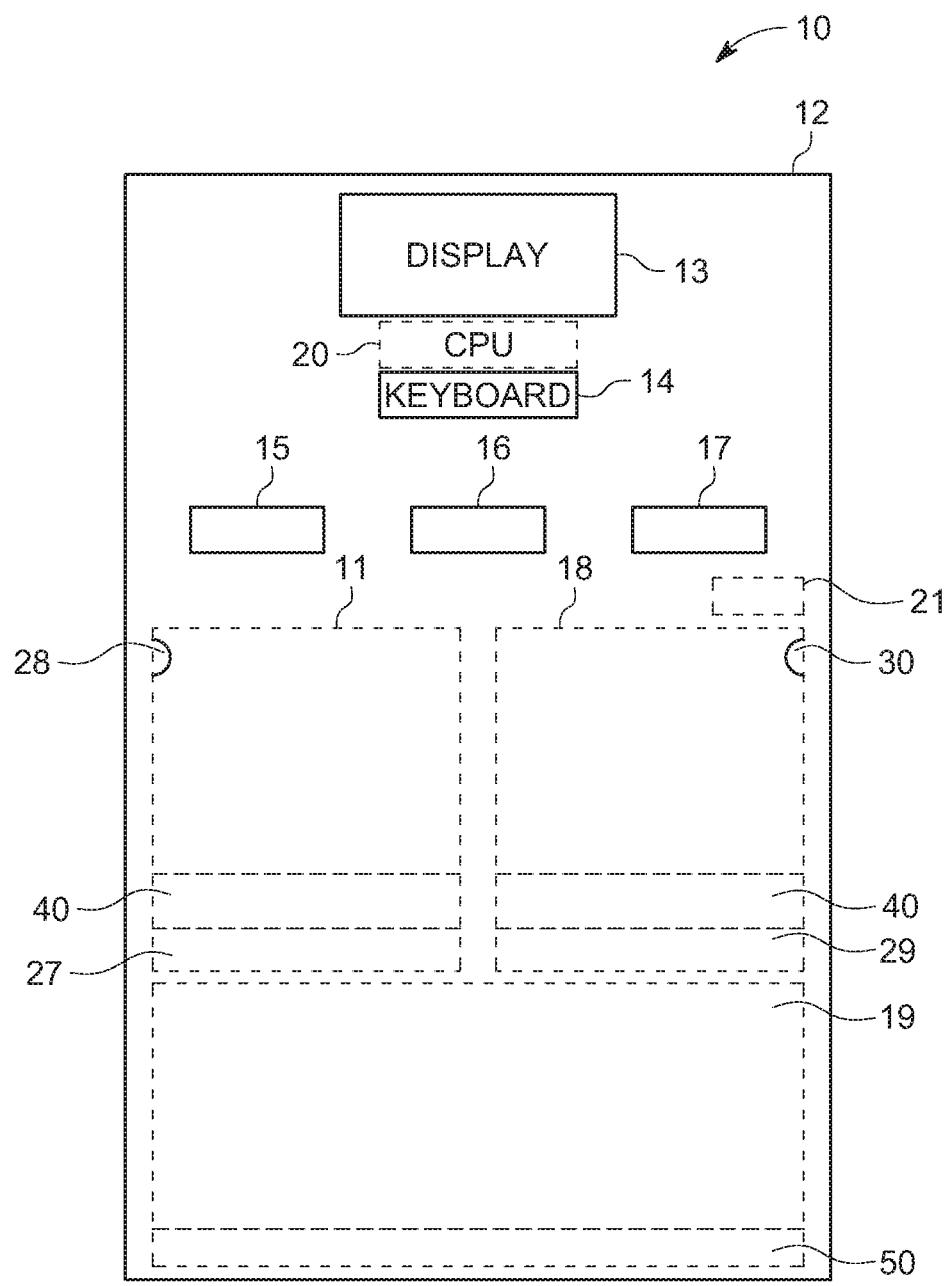
FIG. 1 is front elevational view of the medication disposal and reconciliation device in accordance with principles of the present invention.
Figure 2:
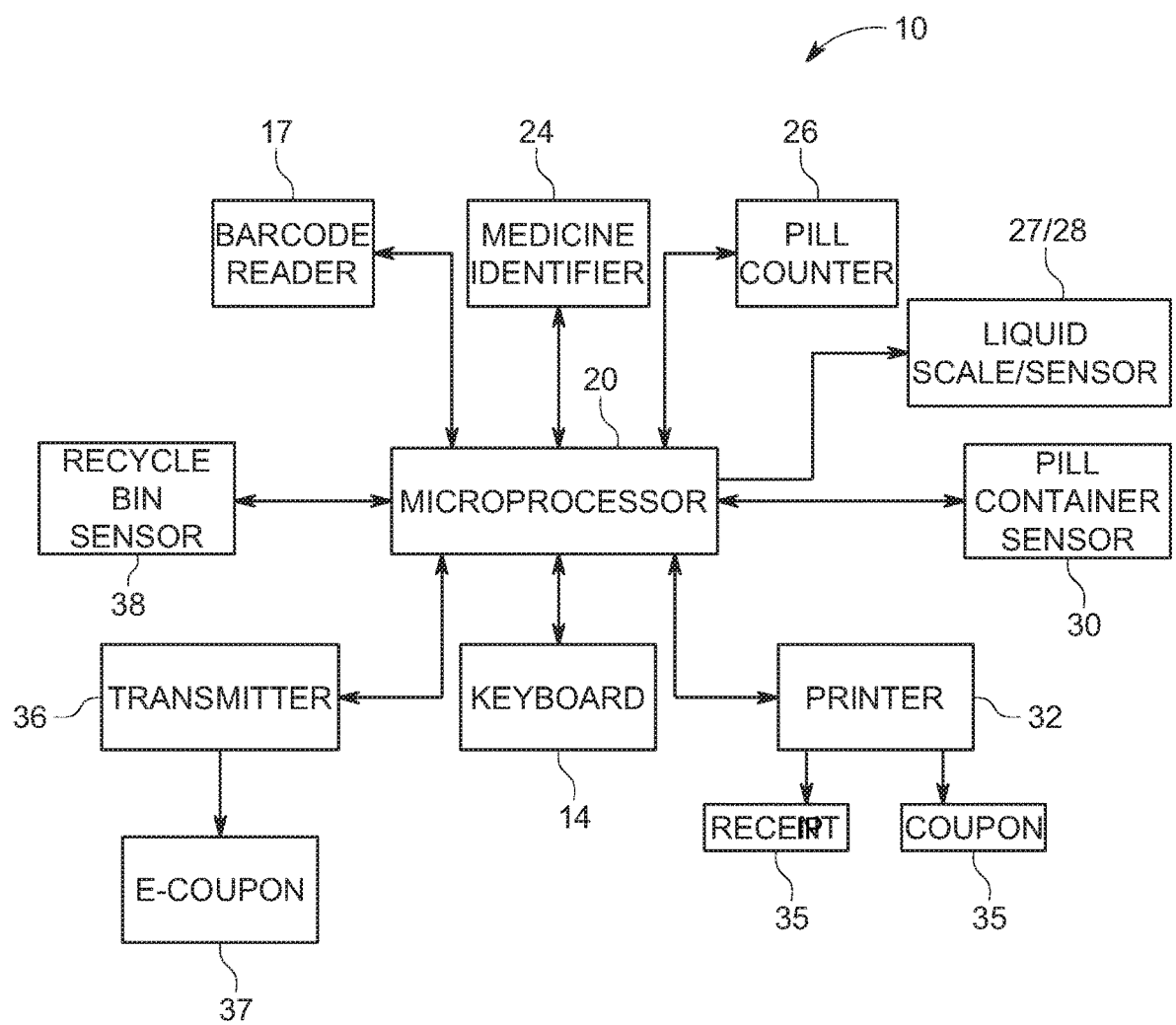
FIG. 2 is a system block diagram of the medicine disposal and reconciliation device in accordance with the instant invention shown in FIG. 1.
Figure 3:
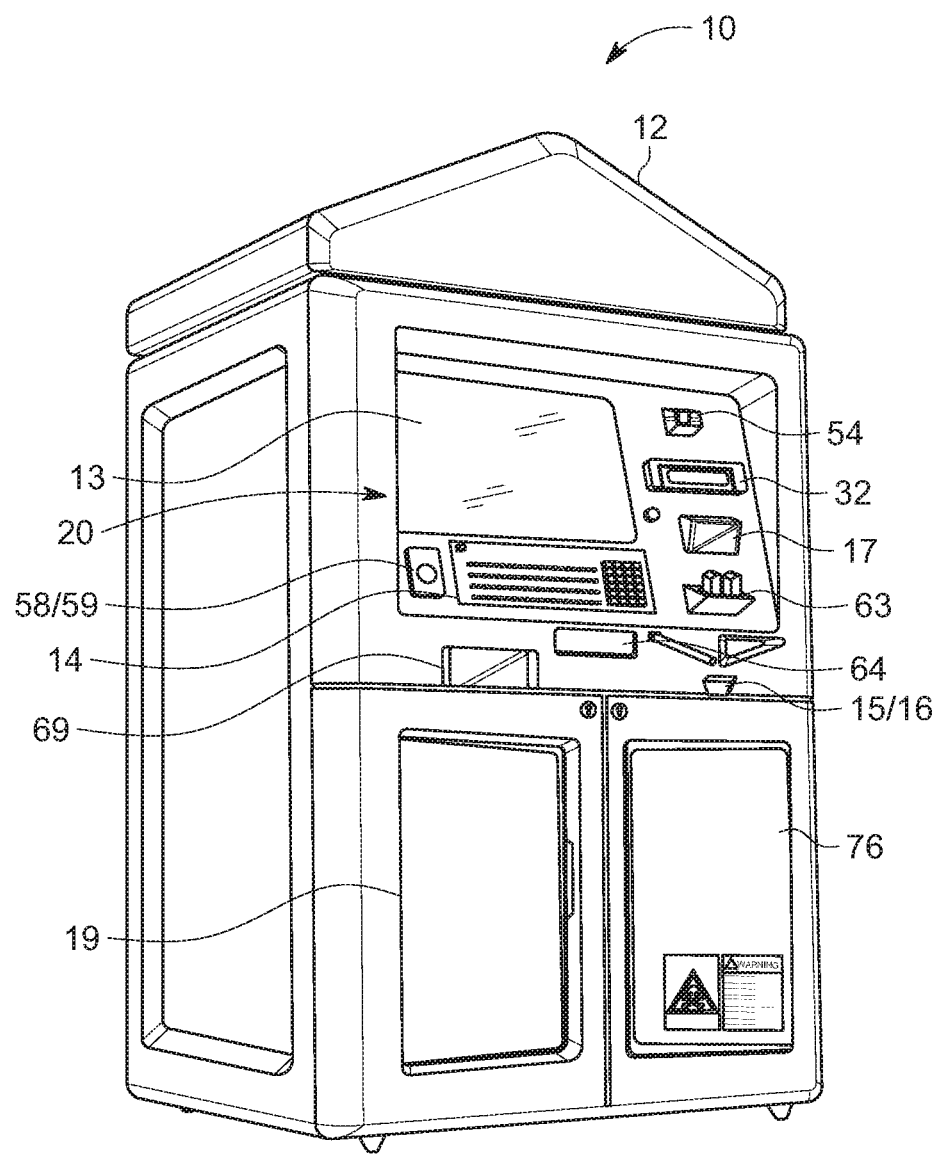
FIG. 3 is a front perspective view of the medication disposal and reconciliation device in accordance with the preferred embodiment.
Figure 4:
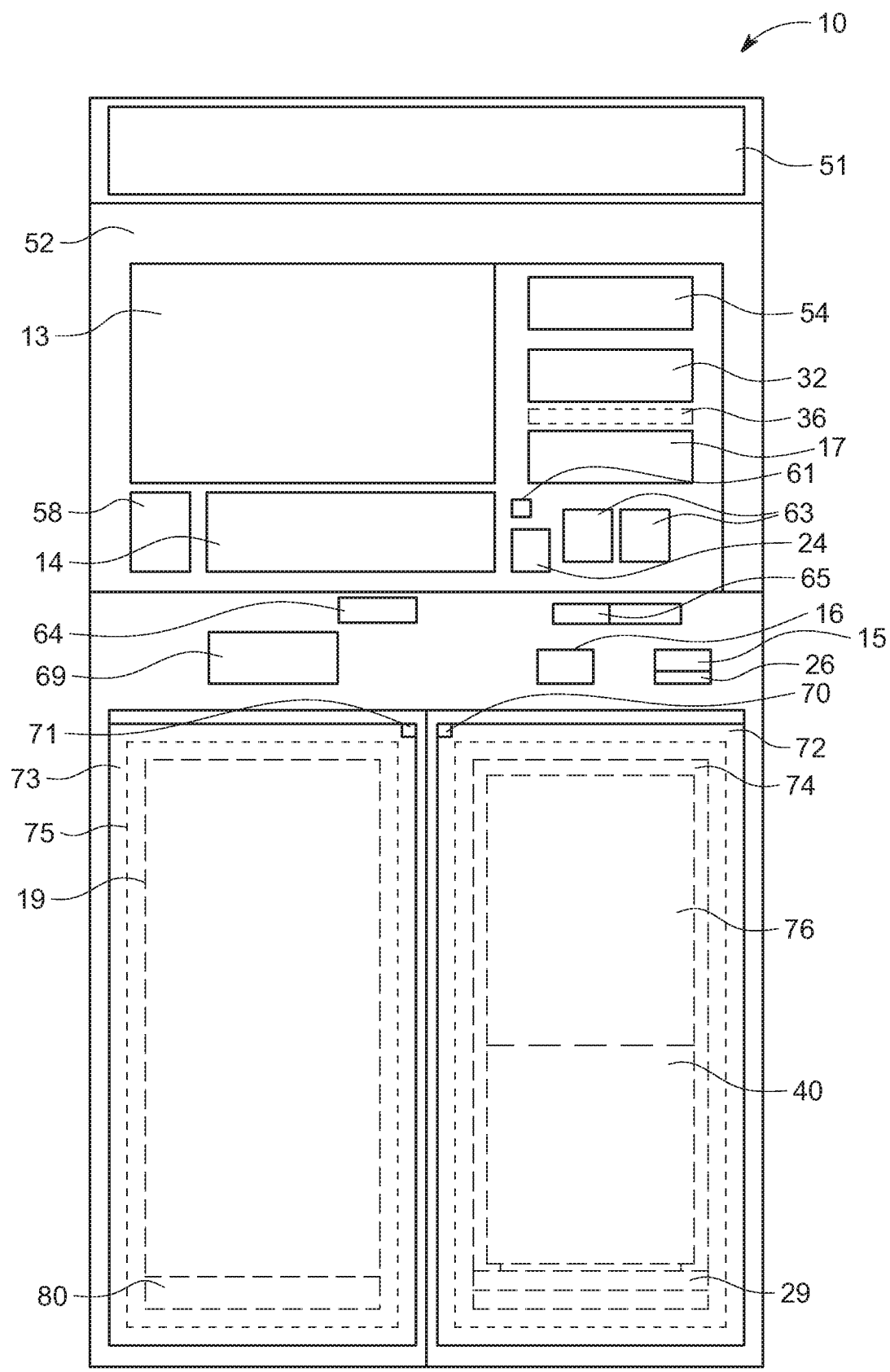
FIG. 4 is a front elevational view of the medication disposal and reconciliation device of FIG. 3 in accordance with the preferred embodiment.
Figure 5:
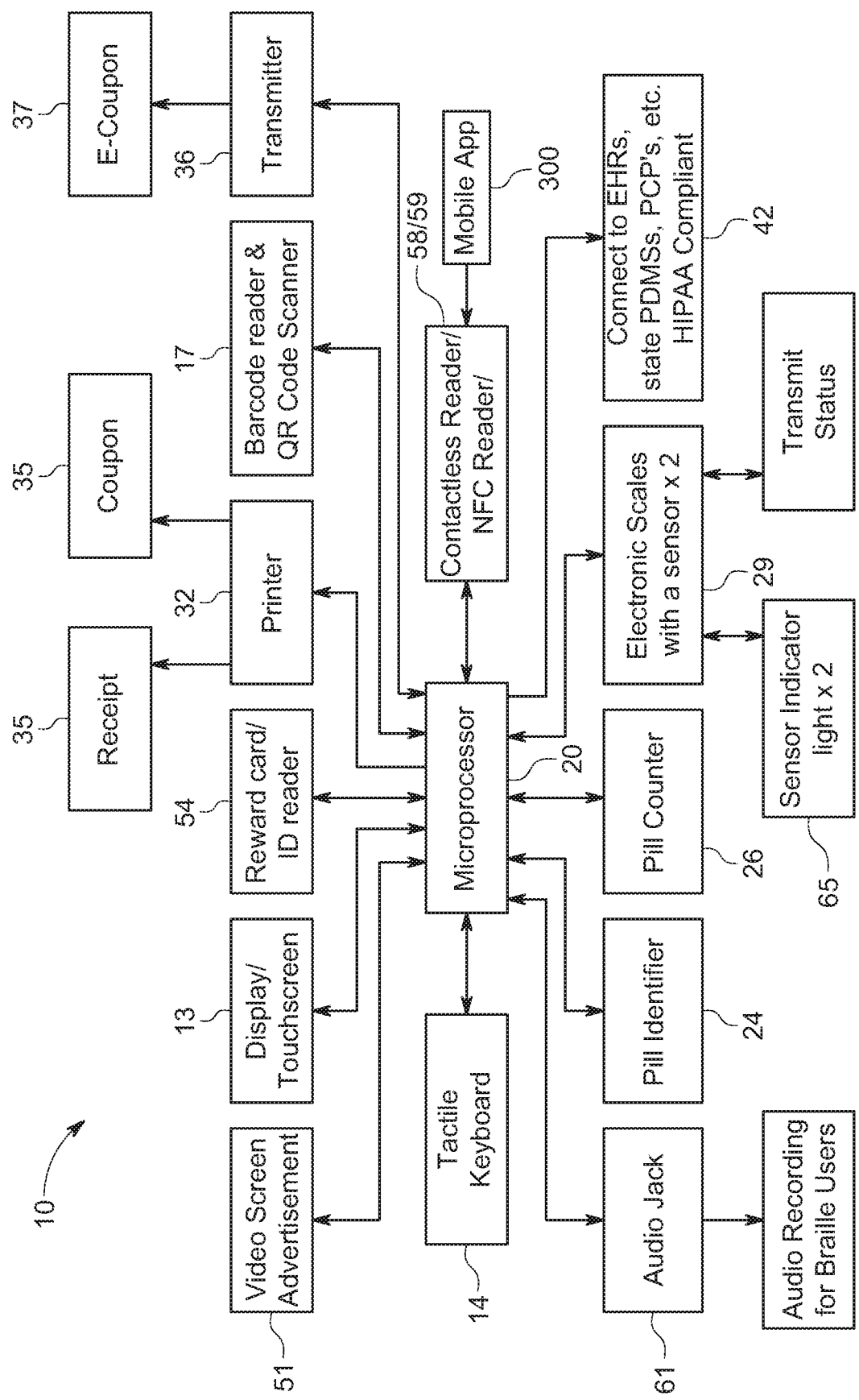
FIG. 5 is a system block diagram of the medication disposal and reconciliation device of FIG. 3 in accordance with the preferred embodiment.

With reference to the drawings in which like reference designators refer to like elements, FIGS. 1 to 7 depict the preferred and alternative embodiments of the instant invention which is generally referenced as a medication disposal, treatment and reconciliation kiosk device, medication disposal kiosk or device and, or by numeric character 10. There is shown in FIGS. 1-7 a medication disposal and reconciliation kiosk device 10 for collecting, disposing, identifying, measuring, counting, reporting and dissolving or diluting medication collected with a biodegradable solution and generating a paper or electronic coupon that can be used to purchase new prescriptions, refills or other items or converted to cash. With reference to FIGS. 1-7, the medication disposal, treatment and reconciliation kiosk device 10 includes a cabinet housing 12, collection container for receiving discarded medication 11/18, barcode reader and QR scanner 17, computer processor 20, keyboard 34, pill counter 26, medicine identifier 24, scale(s) 27/29 for weighing medication, biodegradable safe liquid 40 for dissolving or diluting the medication received in the collection container 11/18, printer 32 for printing a receipt 33 and, or coupon 35, electronic coupon 37, wireless electronic transmission circuitry or devices 36 and a recycle bin 19 for the emptied bottles or containers with a dissolvent 50 that dissolves the ink on the bottle or container labels to remove names and other information. The instant invention 10 also includes a stand-alone kiosk computer processor readable code of instructions 100 for a stand-alone kiosk device 10 and a portable medication disposal and reconciliation computer processor code of instructions 200 for a portable kiosk device 10. The instant invention 10 includes electronics, as shown in FIGS. 2 and 5, for communicating with a variety of electronic medical record systems available or known in the medical records industry or medical industry at large. The medication disposal and reconciliation kiosk device 10 may further include an app 300 for smart phones, androids, iPads and, or other mobile communication devices that facilitates communication with the kiosk device 10 to report data to the device 10, facilitate operation or provide other necessary functions. The app 300 also communicates with the processor readable code 100 and 200 and may embody portions of the code 100, 200. In an alternative embodiment, the instant invention 10 may include a sharp container 21 for depositing syringes, needles or other sharp medical instruments or articles. The kiosk device 10 may also collect and report medication disposal data in real time or as needed.

With reference to FIGS. 1-5, the medication kiosk device 10 comprises a cabinet 12 for supporting keyboard 14, pill medication deposit door 15, liquid medication deposit door 16, barcode scanner 17, pill container 18, liquid medication container 11, liquid medication container scale 27, microprocessor or computer processor 20, recycle bin 19, pill dissolvent 40, medicine identifier 24, pill counter 26, pill container sensor 30, liquid container scale 27, liquid medication container sensor 28, pill container scale 29, printer 32 for printing receipts 33 and coupons 35, transmitter 36 for transmitting electronic coupons 37 and other information to a user, recycle bin sensor 38, liquid dissolvent or diluter 40 and recycle bin dissolvent 50. Referring to FIGS. 3-5, the medication kiosk device and system 10 also includes an advertisement video screen 51 for running advertisements to fund the kiosk 10, encasement for privacy 52, rewards card insert or ID reader, mobile device contactless reader 58, NFC reader 59 for electronic pay apps such as Apple Pay® or Google Pay®, audio jack 61, identity protection roller(s) 63, braille instruction plate 64 for instructing users to plug their headset into the audio jack 61 to hear instructions, status light 65 for disposal chute including compartment scale indicator light which is lit green when compartment is not full and red when it is almost full (such as ¾ full), pill bottle disposal intake port/chute, pill disposal bin independent lock 70 to lock the compartment, pill bottle disposal bin independent lock 71 to lock this compartment, pill disposal lockable door 72, pill bottle disposal lockable door 73, pill disposal bin lockable compartment 74, pill bottle disposal bin lockable compartment 75, pill disposal container 76 with biodegradable dissolvent 40 to dissolve medication, pill bottle recycle bin sensor 80 for determining when almost full or full, and warning signal 81 on pill disposal door panel. Still referring to FIGS. 3-5, the instant invention 10 further includes Wi-Fi®, Bluetooth® or other wireless communication hardware and, or software known for connecting to EHR's, state PDMP's, PCP's, medical providers, pharmacies, IT specialists and other relevant organizations in a manner that is preferably HIPPA compliant. The cabinet 12 preferably has a cabinet door for accessing the components in the cabinet 12. The display 13 is a standard electronic screen, such as a computer monitor, video screen, LED monitor, LCD monitor or flat panel monitor, that communicates with the microprocessor 20 to display a menu, information, instructions and data based on information inputted through the keyboard 14. The microprocessor 20 receives, processes and responds to electronic inputs from the keyboard 14, barcode reader 17, medicine identifier 24, pill counter 26, liquid medication container scale 27, liquid medication container level sensor 28, pill container level sensor 30, printer 32, transmitter 36 and recycle bin level sensor 38. The medication disposal device 10 includes a processor readable code of instructions or software that is processed by the microprocessor 20 for communicating with the user and performing the objects, functions and features of the instant invention as hemin described. The barcode reader 17 reads the barcode on all medication boxes or bottles and records the data in the microprocessor memory and shows the information on the display screen 13 for the user to see. Barcodes for over-the-counter ("OTC") medications may be read, stored and processed by the kiosk device 10 so all OTC medications may be deposited in the kiosk device 10 anywhere in the United States. The barcode reader 17 also can be used to read the barcode on the medical record label if the provider's office wants the user's returned medication information to be a part of the patient's medical record. The barcode reader 17 may also be used to get provider and individual information from the barcode so a message can be sent to the provider and individual user whenever medication that the provider prescribed are disposed of in the medication disposal kiosk 10. Pharmacies may assist to get this information encoded into barcodes. The keyboard 14 allows for inputting information and medication data in response to instructions and questions and navigating through the software program residing in the microprocessor 20. The keyboard 14 may be used if the barcode reader 17 cannot read the barcode to type in the name of the medication as it appears on the medication bottle or container. The medicine/pill identifier 24 will identify the medication that is being deposited based on the letters or numbers engraved on the pill by the manufacture. The pill counter 26 counts the number of pills that a person puts into the kiosk device 10 after scanning the barcode, typing in the name of the pill or using the pill identifier. The pill container sensor 30 or scale 29 determines by a scanned signal or weight when the pill container 18 is almost or ¾ full, and sends a signal indicating that the pill container 18 needs to be removed and emptied. After emptying, pill dissolvent 40 is poured into the pill container 11. The liquid container scale 27 and, or level sensor 28 determines by weight when the liquid medication container 11 is full or nearly full, such as ¾ full, and sends a signal indicating that the liquid medication container 11 needs to be removed and emptied. As some liquid medications are thick and water based or thin and oil based, the liquid medication container 11 may include a deposit bag into which liquid medication is poured. The kiosk device 10 may include a funnel at the opening to the liquid medication container 11 for guiding fluids into the container. The liquid medication bag has structure for automatically sealing the bag when pouring is complete or the bag is nearly full. After a bag is sealed it is weighed by the container scale 27 and recorded before it is dropped into the bottom of the kiosk 10 where it is dissolved.

Referring to FIGS. 1-5, after emptying, liquid dissolvent or diluter 40 is poured into the liquid container 11. All the pharmaceutical waste product is monitored and send a signal is sent from the transmitter 36 and, or to the display 13 when the kiosk is ¾ full, full or nearly full so the waste product may be removed. The dissolvent or diluter 40 is a bio-degradable/green-safe liquid that is poured in the liquid medication container 11 or pill container 18 at the bottom of the cabinet 12 where the liquid medication and, or pills are dropped to dissolve or dilute the medication so the containers 11, 18 can be safely emptied and discarded.

Still referring to FIGS. 1-5, the printer 32 and transmitter 36 allow for providing printed or electronic receipts 33 and redeemable coupons 35, 37 and the recycle bin 19 allows for discarding and recycling emptied medicine bottles, boxes and other container types. A user can have an option to receive a printed or electronic receipt 33, or both, that lists the type and amount of medications disposed and deposited in the kiosk device 10. The printer 32 prints the receipt 33 while the transmitter 36 transmits an electronic receipt to the user. The user also has an option of a printed coupon from the printer 32 or an electronic coupon 37 sent by the transmitter 36 that can be redeemed at a pharmacy when they purchase their next prescription or over-the-counter medication or for any other in-store purchase at the store location of the kiosk device 10 or the coupon 35/37 may be redeemed for cash or credit. A higher coupon incentive/amount can also be given whenever opioids and other controlled substance are disposed and when individuals choose vendor coupons as their incentives which will encourage healthcare provider and retail pharmacy partnerships, etc. The transmitter 36 has high tech IT capabilities that can electronically transmit and send coupons 37 and, or receipts 35 or other information to the user via Bluetooth, email, text, or other message transmissions means directly to a provider/prescriber, into an electronic health record of the person whose prescription was disposed of, to a state's prescription drug monitoring program (PDMP), to a centralized computer anywhere in the US or in the world so that data can be collected and maintained per HIPAA compliance or guidelines. Information transmitted may be date and time stamped and include, but not be limited to:

a. the name of the medications disposed, b. the number of pills disposed, d. how much money was given in coupons from the kiosk for the disposed medication, e. the provider's name who prescribed the medication, f. the pharmaceutical company that made the medication, etc.

The recycle bin 19 provides a depository for the emptied plastic medication bottles and cardboard boxes. The recycle bin 19 will be locked and the patients placing the bottles in the recycle bin will be reminded to remove the label from their prescription bottles or to use the identity theft stamp located on the kiosk to black out their name and medication information before placing their pill bottles into the recycle bin. The contents of the recycle bin can then be recycled, thus keeping these plastic pill bottles out of our land fields and leading to a healthy green planet. Also, if possible, if the is a financial gain from the recycling of the pill bottles, maybe this money could be used to go back into the kiosk incentive program, thus benefiting those disposing of their medications.

Still referring to FIGS. 1-5, the instant invention 10 provides for various economic methods for paying for or underwriting implementation of the medication disposal device 10 of the instant invention. Pharmacy chains can buy kiosks for their stores, community partners, EMS, community health workers, provider's offices, community centers, senior centers, etc. where the kiosk will be located, and the printed coupons generated by the kiosk will be coupons to be used in their chain of pharmacies/stores. The individual will have an option to receive store or vendor coupons or a coupon that can be redeemed for cash (each coupon will have a unique coupon number). If they choose a vendor coupon that can be redeemed for cash, then it will be redeemed at the store and the store/pharmacy, thus increasing the likelihood that the individual will spend the cash in the store/pharmacy where they go to cash in the coupon. Individuals may also choose to receive cash via Cash App or PayPal, but this amount will be less than if they had chosen a vendor's coupon. This is done, to encourage individuals to use their financial incentives to purchase newly prescribed medications, refill their medications, etc. thus decrease the cost of medications for the individual and the incidence of medication noncompliance and the long-term medical complications that are associated with medication noncompliance. Retail pharmacy chains and hospital outpatient pharmacies can partner with community partners, EMS, community health workers, provider's offices, community centers, senior centers, etc. where the kiosk is located or will be used, so that the kiosk can generate coupons for a particular pharmacy, which will then cause individuals to go to that pharmacy to fill their new prescriptions or refills in order to redeem the coupon generated by the kiosk, thus increasing/generating revenue for the pharmacy and other revenue as the individual goes shopping for other items while in the store. All the pharmaceutical companies can contribute into a governmental escrow account a certain amount of money every year that will be used to pay for the disposal of the bio-degradable solution/mixture, disposal of the dissolved medications and the coupons generated by the kiosks. Or the pharmacy chain can pay for the disposal of the bio-degradable mixture and its own coupons, since the coupons will be used in their pharmacy/store and while the individual is there to redeem the coupon, he/she will most likely purchase other products from the store. Because the Opioid Epidemic is a major crisis, to encourage individuals to dispose of controlled substances and opioids, all disposed controlled substances and opioids will result in a higher coupon amount being generated by the kiosk for the individual disposing them. As the government helped hospitals and provider offices purchase EHRs, maybe a similar plan can be put in place to help provider offices, ALFs, Senior Community Centers and other locations obtain kiosks for their outpatient locations commonly visited by seniors and others who often fill prescriptions, often have medication dosages changed and who often need to dispose of old medication or medication they am no longer taking.

The dissolvent and, or dilution solutions 40 and 50 of the instant invention 10 are preferably biodegradable. The instant invention 10 includes methods for disposing of the dissolvent and dilution and other solutions per the protocol set by each state as to how hospitals and pharmacist should dispose of pharmaceutical waste or byproducts or the use of any bio-degradable product. Each kiosk device 10 will send a signal when a certain weight of pharmaceutical waste or products have been disposed in each kiosk. A disposal company will be notified and will go to the location of the kiosk, empty the pharmaceutical waste and dispose of it per the state protocol. The disposal company will also refill the kiosk with the necessary liquid whenever they empty the kiosk. Because the name of the pills being disposed and the pharmaceutical company that made each pill will be recorded, this information will be available each in a timely fashion (quarterly, biannually, annually) for pharmaceutical companies to review, for the DEA, CDC and other entities who would benefit from this information. This information will also be important when asking pharmaceutical companies to pay for disposal of the pharmaceutical waste product if that option is used. The procedure for disposing of medications into the medication disposal and reconciliation kiosk will vary slightly by where the kiosk is located and whether the kiosk is the Stand-alone or the Portable kiosk.

With further reference to FIGS. 1-5, the medication disposal and reconciliation kiosk device 10 includes wireless or wired telecommunication or communication electronics for communicating with each state's Prescription Drug Monitoring Program ("PDMP") for tracking, identifying and reconciling legal and control substances deposited in the kiosk device 10. The kiosk device 10 may have a database or access to a database for each state that contains all authorized medication providers or prescribers, such as prescribing providers, physicians, ARNP, podiatrist, dentists and others, in the system so that information can be sent to the provider that wrote the prescription when the medication is deposited in the kiosk device 10. This would improve patient care as the provider would be able to call or contact the patient to confirm and determine the reason for disposing of the medication, such as there was a change in provider, care, condition or other reasons.

As noted, the instant invention 10 is designed communicate with each state's PDMP. According to the National Alliance for Model State Drug Laws ("NAMSDL"), a PDMP is a statewide electronic database that collects designated data on substances dispensed in the state. The PDMP is housed by a specified statewide regulatory, administrative or law enforcement agency. The housing agency distributes data from the database to authorized individuals under state law that may receive the information for purposes of their profession. PDMP's are important to identify, deter or prevent drug abuse and diversion, inform or advance public health initiatives through outlining drug use and abuse trends while facilitating and encouraging the identification, intervention and treatment of persons addicted to prescription drugs. Currently, forty-nine (49) states have PDMP's that are operational. They monitor controlled substances as defined by federal and state-controlled substances laws and most collet federal schedules II-IV. Florida's PDMP is known as E-FORCSE (Electronic-Florida Online Reporting of Controlled Substance Evaluation Program). The medication disposal and reconciliation kiosk device 10 can also save lives by keeping people from taking medications that lose their efficacy or have become poisonous after expiration.

Figure 6:
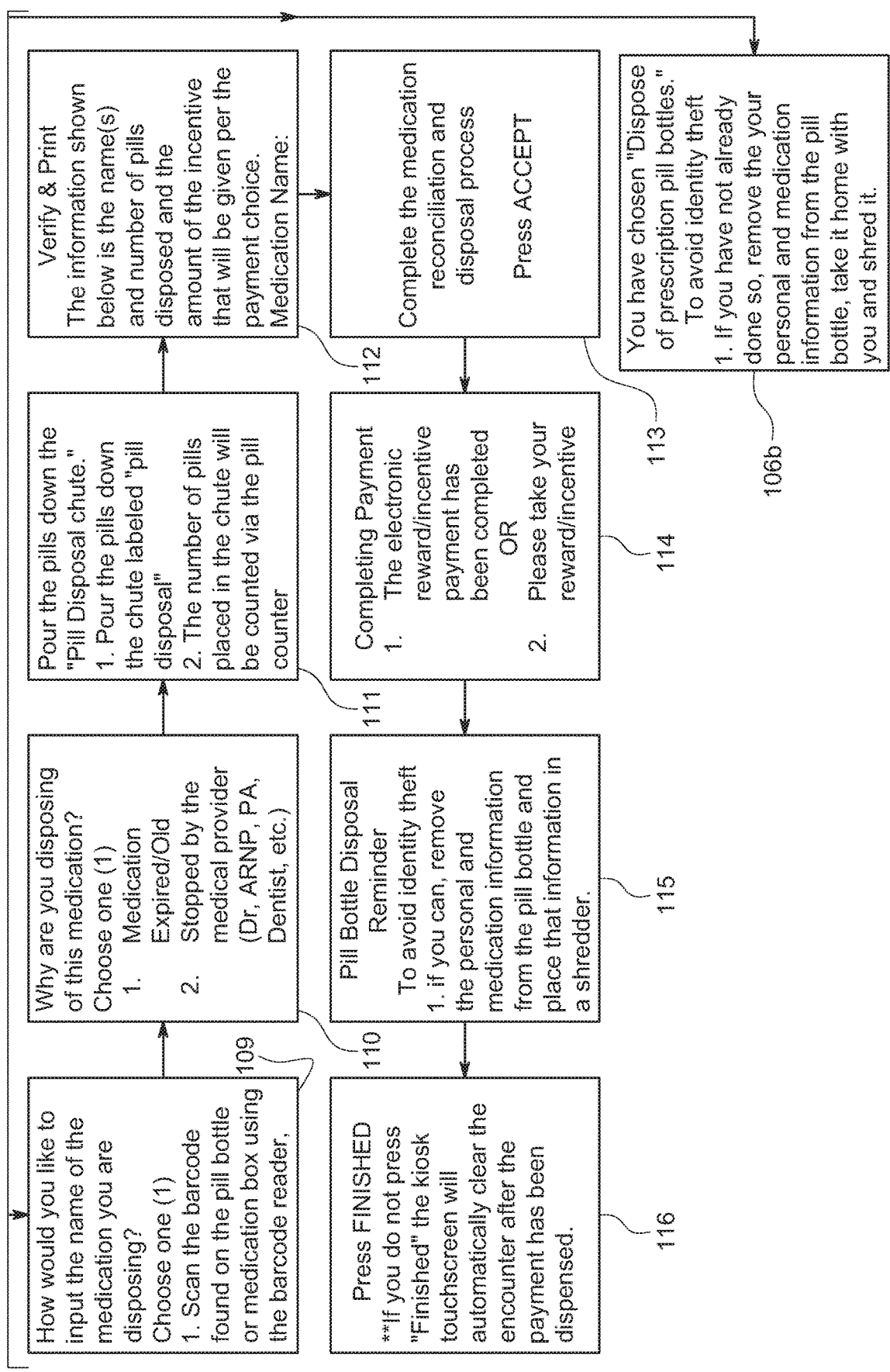
FIG. 6 is a flow chart of the software and system logic of the stand-alone kiosk device of FIG. 3 in accordance with the preferred embodiment.
Figure 6:
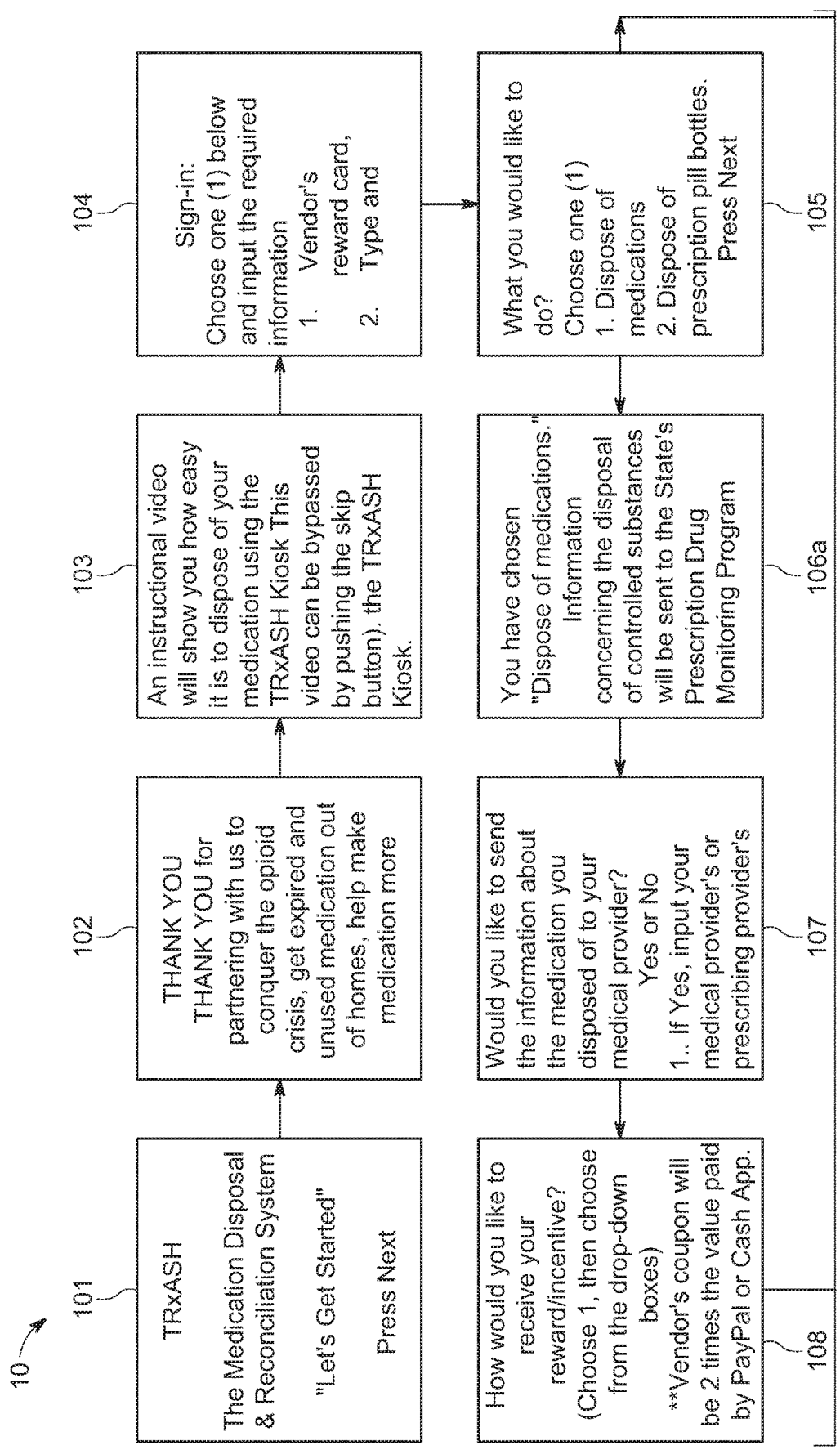

With reference to FIG. 6, the instant invention 10 includes the stand-alone kiosk processor readable code of instructions 100 which performs steps according to inputs or demands by users or preprogrammed instructions. The stand-alone code of instructions 100 includes the following steps, instructions and processes and begins with the TRxASH™ kiosk device 10 inviting the user to get started with a message similar to "Let's Get Started" and "Press Next" 101. The next prompt is similar to "Thank you for partnering with us to conquer the opioid crisis by getting expired or unused medication out of homes, help make medication more affordable, help maintain a healthy planet and hopefully decrease healthcare costs as we all stay healthy and live long happy lives" 102. An instructional video may then be shown illustrating the ease of disposing medication using the kiosk 10 wherein the video may be bypassed by pressing a SKIP button 103. The user then initiates Sign-In and chooses to input a Vendor's reward card or type sign-in information 104. The user is queried to choose one (1) from the following or something similar and to input the information, such as follows: "1. Vendor's reward card; 2. Type and input your username and password; 3. Contactless device: Use your cell phone at the contactless device, etc. (personal accounts can be set up via the TRxASH™ mobile app); 4. As an anonymous user: signing in anonymously" and proceed; 5. Create a new account: Enter your name, DOB, email address, username & password; or 6. Braille Instructions: If assistance is needed for those who may need the assistance of braille, instructions in braille are located on the kiosk under the keypad, a telephone number is listed and a port for headphones is available to assist the user." The user is then instructed to "Press Next" 104. The user is then prompted to indicate if they are depositing medications or medication/prescription bottles 105. If they are only depositing bottles, they are directed to avoid identity theft by removing labels from medication bottles, applying an identity theft prevention stamp provided, black out information with marker, and thereafter to dispose of bottle in recycle bin through bottle recycle chute 106b. If depositing medication, it is confirmed that the user selected to deposit medication and information may be provided regarding controlled substance information being sent to state agencies 106a. For instance, a message such as the following may be displayed as follows: "You have chosen "Dispose of Medications." Information concerning the disposal of controlled substances will be sent to the State's Prescription Drug Monitoring Program (PDMP) as we all work together to get expired and unused controlled substances out of our homes and off the streets as a way to combat the opioid crisis. You can dispose of controlled substances via this kiosk by using your profile & account or anonymously, if this kiosk is located in a hospital/clinic where there is an on-site pharmacy, a retail pharmacy, a law enforcement office, narcotic treatment programs or an Assistant Living Facility and you are an ultimate user (the person who was prescribed the medication and/or a household member of the person or pet who was prescribed the medication and/or any person lawfully entitled to dispose of a deceased person's property) as stated in the Drug Disposal Act. If this kiosk is not located in one of the above locations, please do not dispose of controlled substances in this kiosk but dispose of them in one of our kiosks located in one of the locations mentioned above. Thereafter, the user is asked if they would like to send information regarding the medication disposal to their medical provider, and if 'yes' they input medical provider information 107. The user is then queried on how they would like to receive their reward or incentive by choosing from a drop box which may include choices such as paper or electronic pharmacy coupon, hospital/clinic credit, payment via PayPal which requires account information or payment into a cash app such as Cash App before pressing "Next" 108. The user is then asked to enter the name of the medication being deposited by typing it in, entering the pill identifier information or scanning the barcode on the medication bottle, box or container 109. The user is then asked why they are discarding the medication by asking them to select from a menu, such as, medication expired, no longer required or stopped by the user's medical provider, had an adverse reaction, therapy was completed, alternate therapy administered, a change in dose, deceased or other 110. The user is then instructed to pour the medication down the appropriate chute 111, such as the chute labeled "Pill Disposal" for pills. If pills are poured down the chute, then they will be counted by the pill counter. This step may be repeated as necessary. Once done, the user presses Next 111. The name and number of pills deposited, and the user incentive am then verified and printed 112. The verified and printed information may include medication name, number of pills, reward/incentive amount and type, controlled substance disposal query, name (optional), number (optional), informed information will be sent to state's Prescription Drug Monitoring Program (PDMP) and, or a query for a printout 112. The user then presses NEXT. Thereafter, the user is queried if they have completed the medication disposal process, and if so, they press ACCEPT 113. The reward/incentive payment process is then completed and provided to the user 114. The user is then reminded to avoid identity theft by removing labels from medication bottles, applying an identity theft prevention stamp provided, black out information with marker, and thereafter to dispose of bottle in recycle bin through bottle recycle chute 115. When the user is done, they press FINISHED and the program ends, and screen cleared 116.

Figure 7:
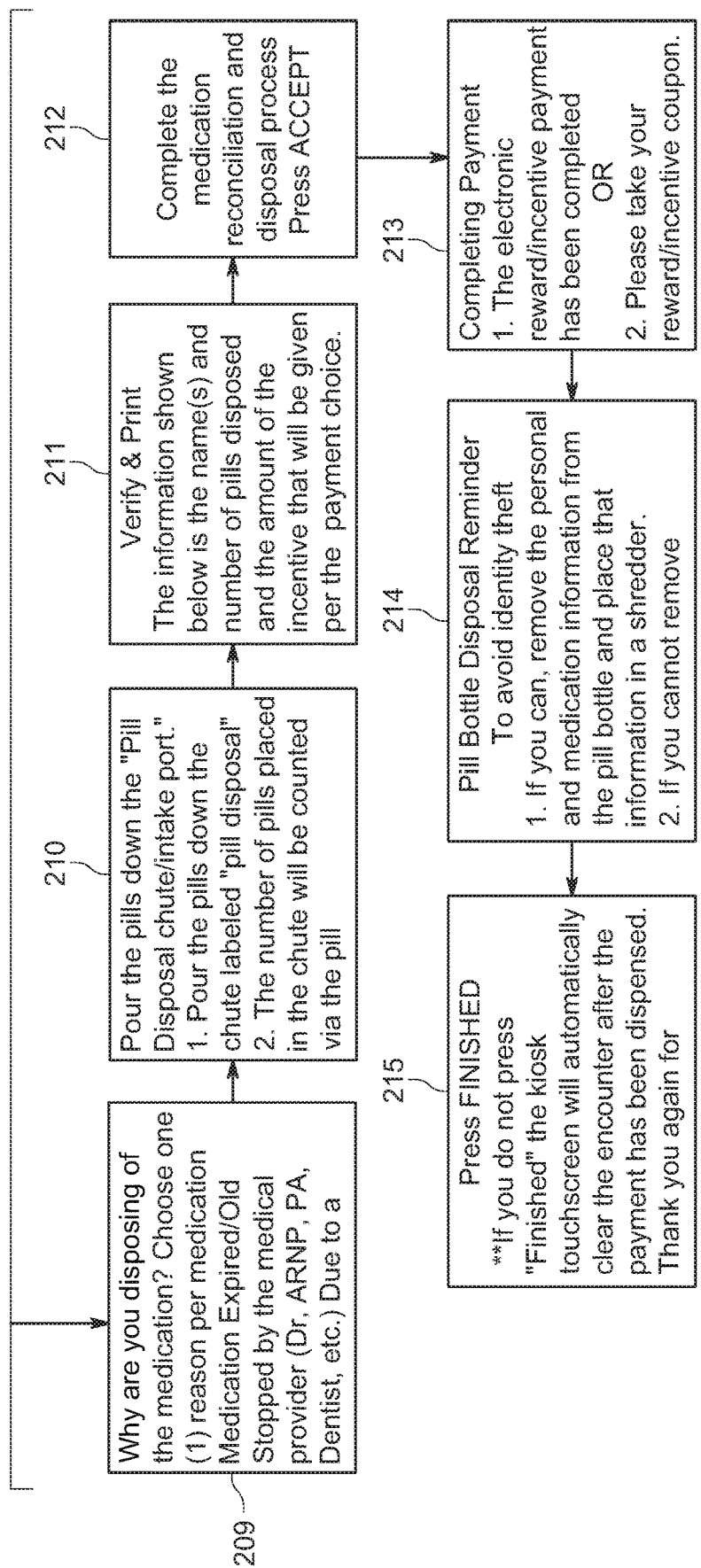
FIG. 7 is a flow chart of the software and system logic of the stand-alone kiosk device of FIG. 3 in accordance with the preferred embodiment.
Figure 7:
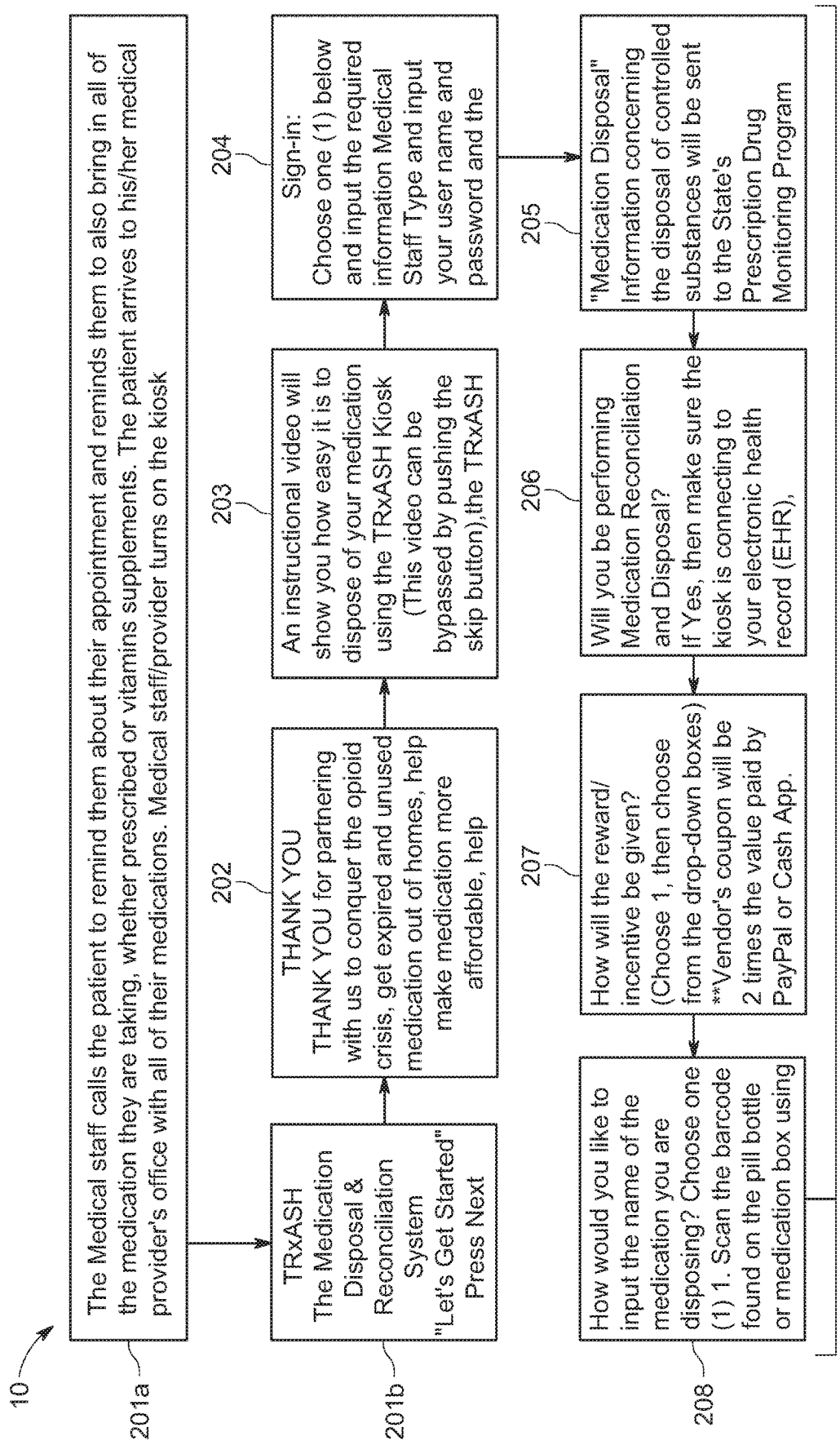

With reference to FIG. 7, the instant invention 10 includes the portable kiosk processor readable code of instructions 200 which performs steps according to inputs or demands by users or preprogrammed instructions. The portable kiosk code of instructions 200 includes the following steps, instructions and processes and begins with the TRxASH™ kiosk device 10 inviting the user to get started with a message similar to "Let's Get Started" and "Press Next" 201. The next prompt is similar to "Thank you for partnering with us to conquer the opioid crisis by getting expired or unused medication out of homes, help make medication more affordable, help maintain a healthy planet and hopefully decrease healthcare costs as we all stay healthy and live long happy lives" 202. An instructional video may then be shown illustrating the ease of disposing medication using the kiosk 10 wherein the video may be bypassed by pressing a SKIP button 203. The user then initiates Sign-In and chooses to input a Vendor's reward card or type sign-in information 104. The user is queried to choose one (1) from the following or something similar and to input certain information, such as follows: "1. Medical Staff—type and input your name and password and the patient's or client's medical record number; 2. Established user with an account; 3. Type in your user ID and password: 4. Contactless device 58: Use your cell phone at the contactless reader device or set up or use personal account via TRxASH™ mobile app; 5. As an anonymous user; 6. Create anew account by entering name, DOB, email address, username and password; or 6. Braille Instructions: If assistance is needed for those who may need the assistance of braille, instructions in braille are located on the kiosk under the keypad, a telephone number is listed and a port for headphones is available to assist the user" 204. The user is then instructed to "Press Next" 204. The next step is Medication Disposal wherein the user is informed that information concerning the disposal of controlled substances may be sent to state agencies 205. For instance, a message such as the following may be displayed as follows: "You have chosen Medication Disposal. Information concerning the disposal of controlled substances will be sent to the State's Prescription Drug Monitoring Program (PDMP) as we all work together to get expired and unused controlled substances out of our homes and off the streets as a way to combat the opioid crisis. You can dispose of controlled substances via this kiosk by using your profile & account or anonymously, if this kiosk is located in a hospital/clinic where there is an on-site pharmacy, a retail pharmacy, a law enforcement office, narcotic treatment programs or an Assistant Living Facility and you are an ultimate user (the person who was prescribed the medication and/or a household member of the person or pet who was prescribed the medication and/or any person lawfully entitled to dispose of a deceased person's property) as stated in the Drug Disposal Act. If this kiosk is not located in one of the above locations, please do not dispose of controlled substances in this kiosk but dispose of them in one of our kiosks located in one of the locations mentioned above. The user then presses Next 205. Thereafter, the user is asked whether they will be performing Medication Reconciliation and Disposal, and if 'yes' then they am told to and then make sure the kiosk 10 is connecting to their electronic health record (EHR) and, if 'no' they press Next. The user is then queried on how they would like to receive their reward or incentive by choosing from a drop box which may include choices such as paper or electronic pharmacy coupon, hospital/clinic credit, payment via PayPal which requires account information or payment into a cash app such as Cash App before pressing "Next" 207. Before the selection is made the user is advised that coupons are twice the value paid by PayPal or Cash App 207. The user is then asked to enter the name of the medication being deposited by typing it in, entering the pill identifier information or scanning the barcode on the medication bottle, box or container 208. The user is then asked why they are discarding the medication by asking them to select from a menu, such as, medication expired, no longer required or stopped by the users medical provider, had an adverse reaction, therapy was completed, alternate therapy administered, a change in dose, deceased or other 209. The user is then instructed to pour the medication down the appropriate chute 210, such as the chute labeled "Pill Disposal" for pills. If pills are poured down the chute, then they will be counted by the pill counter. This step may be repeated as necessary. Once done, the user presses Next 210. The name and number of pills deposited, and the user incentive are then verified and printed 211. The verified and printed information may include medication name, number of pills, reward/incentive amount and type, controlled substance disposal query, name (optional), number (optional), informed information will be sent to state's Prescription Drug Monitoring Program (PDMP) and, or a query for a printout 211. The user then presses NEXT. Thereafter, the user is queried if they have completed the medication disposal process, and if so, they press ACCEPT 212. The reward/incentive payment process is then completed and provided to the user 213. The user is then reminded to avoid identity theft by removing labels from medication bottles, applying an identity theft prevention stamp provided, black out information with marker, and thereafter to dispose of bottle in recycle bin through bottle recycle chute 214. When the user is done, they press FINISHED and the program ends, and screen cleared 215.

Referring to FIGS. 1-7, the script and procedure for a provider or specialist office visit and methods for using the instant invention 10 may go as follows. To use the kiosk device 10, the user may register to establish an account with a username and password or simply login with their username and password. The user may then enter the type of medication and the prescribing physician of the medication being disposed into the kiosk device 10. Alternatively, the user may choose to be anonymous when disposing medication into the kiosk device 10.

Still referring to FIGS. 1-7, an Office Staff call to the patient prior to the provider's visit may go as follows:

"Hi, I am calling to remind you about your appointment tomorrow. Also, can you please bring with you all the medications that you are presently taking, prescribed medications, vitamins, and herbal supplements and any medication that you am no longer taking? You can dispose of your old medications hem at the office in the TRxASH™ kiosk and receive a printout or coupon that you can use when you pick up your new prescriptions or turn it in for cash."

Procedure when the patient arrives for the provider's appointment:

MA (medical assistant): Asks the patient what medication he/she is presently taking and am there any additional medication that the patient has taken over the last 30, 60 or 90 days since he/she last saw the doctor. Specifically, has he/she been prescribed any pain medication or any new medication by a specialist or the ER that they did not bring into the office today.

MA: Reviews all the medication that the patient is presently taking with the patient and records them in the EHR. The MA then places the medications that the patient is taking in a blue bag, closes it and places the patient's MR/registration sticker on the bag & gives it back to the patient. The old medications that the patient wishes to place in the kiosk is then reviewed with the patient to make sure that no medication that the patient is presently taking is in that group of medicines. The medications that the patient wishes to be discarded in the kiosk are placed in a red bag, the patient's MR/registration sticker is placed on the bag, the bag is scaled, and the red bag is also given back to the patient. Both bags are put in the room with the patient as he/she waits to see the PCP/provider.

Provider: When the provider sees the patient, the provider will review the medications in both bags.

Provider: During the patient's office visit, if the provider decides to prescribe a new medication, change the dosage of a medication that the patient is already taking, and/or discontinue one of the medications that the patient is presently taking, the provider will inform the patient and remove the discontinued medication that he/se wants the patient to discontinue and place it in the red bag.

Provider: Once the final decision about the patient's medications has been discussed with the patient and the patient understands all medication changes, what new prescriptions he/she will be picking up from the pharmacy, what medications are being discontinued and discarded, the PCP/provider will dispose of the discontinued medications into the portable TRxASH™ kiosk him/herself or give the red bag to the MA who will then dispose of the discontinued medications via the portable TRxASH™ kiosk while in the room with the patient. Also, to ensure compliance with the Drug Disposal Act, controlled substance will only be disposed in the TRxASH™ kiosk that is located in designated locations and only by ultimate users as defined by the Drug Disposal Act. If the Drug Disposal Act is amended and/or legislative changes are made, these changes will be accepted and made.

The Procedure for disposing medications into a medication disposal & reconciliation kiosk 10 in the PCP/Provider's office can be as follows but will be determined by the protocol or flow of each individual provider's office:

1. To dispose of the medications in the portable TRxASH™ kiosk, the Provider or MA will sign-into the kiosk using their preestablished log-in and passwords.
2. The Medical Provider or MA will choose how they wish to input the name of the medication; either using the barcode scanner, the pill identifier or the tactile keyboard.
3. After the name of the medication has been inputted, for example by using the barcode on each prescription bottle or on the OTC bottle/box, the Medical Provider/MA will then input the reason why each medication is being disposed of, ex. discontinued by PCP, change in dosage, treatment completed, etc.
4. After inputting the information for a medication, he/she will empty the content of each bottle/box into the kiosk one by one. Ex. Barcode scan→reason for medication disposal→empty pills into kiosk pill disposal chute→pills are counted→information is recorded by the kiosk and transferred into the patient's HER. Next medication→barcode scan→reason for medication disposal→empty pills into the kiosk→pills am counted→information is recorded by the kiosk and transferred into the patient's EHR. This process can be repeated as many times as necessary until all expired, discontinued or unused medication has been disposed of.
5. The kiosk will record the name of each medication and count the number of pills disposed.
6. Once all the medication has been discarded, the MA will verify the disposed medication information on the kiosk's touch/display screen, make sure that it has electronically been sent to the patient's EHR and if the patient desires, will print and give the patient a list of the medications and the number of pills disposed, as well as the amount of the financial incentive. A paper coupon will also be generated. If the patient does not want the information printed, then the MA will electronically send the financial incentive via E-coupon to the patient's choice of payment.
7. The MA will then remove or have the patient remove the label from the pill bottles and shred the labels. If the labels cannot be removed, the MA or individual will blacken out the individual's name and medication information on the label before disposing of the pill bottle in a nearby recycle bin.
8. The MA will press the "FINISH" once the medication reconciliation, disposal and financial incentive process has been completed. The kiosk touch/display screen will then be cleared of all information.
9. The patient will take the printed coupon to the pharmacy or upon arriving at the pharmacy, their financial incentive will be in the pharmacy's system. The patient will be able to use the financial incentive to purchase a new prescription, over-the-counter medication or anything else in the store that he/she may need.
10. Please review the attached flowchart for use of the portable TRxASH™ Kiosk for medication disposal and reconciliation With reference to the flowchart for use of the stand-alone TRxASH™ Kiosk for medication disposal, the procedure for dispensing medications into a Stand-alone TRxASH™ kiosk at any hospital/clinic outpatient or retail pharmacy, in a drug treatment center, law enforcement office, an ALF, etc. is as follows:

1. In accordance with the Drug Disposal Act, anyone will be able to dispose of old or discontinued prescription or over the counter medications at any time using the TRxASH™ kiosk. Individuals will be able to dispose of medications by using vendor reward accounts, accounts/profiles they set-up, or anonymously. However, the disposal of controlled substances by anyone, will be by the ultimate user, as designated by the Drug Disposal Act.
2. The individual will take their medications and/or pill bottles to the TRxASH™ kiosk and review the instruction on the touch/display screen.
3. They will have the option of disposing of the expired and unused medications and pill bottles once they have disposed of their medications, or just their empty pill bottles for recycling if they have taken all of their medications.
4. They will have the option of signing-into the kiosk using their vendor reward card, preset-up account using the contactless/NFC reader (smartphone-TRxASH™ App), the tactile keyboard or by getting instructions for braille users by using their headsets and connecting to the audio jack.
5. Once they have signed in, they will be asked to choose how they would like to receive their financial incentive. They will have an option of receiving paper or electronic coupons for a vendor, vendor's pharmacy, hospital or clinic pharmacy, PayPal, Cash App, etc.
6. If they choose to dispose of their medication, a statement will appear on the touch/display screen notifying them that if they are disposing of controlled substances that information concerning the controlled substance disposed of will be sent to the State's PDMP and that disposal of the controlled substance must be done in accordance with the Drug Disposal Act.
7. They will then be asked to input the name of each medication they are disposing by using the barcode scanner, the tactile keyboard or the pill identifier.
8. Using the touch/display screen, they will also be asked to choose the reason why the medicine is being disposed and will have options like medication expired, stopped or discontinued by my medical provider, therapy completed, user deceased, change in dose, etc.
9. They will also have a chance to input the prescribing physician's information into the system, then a note can be sent to the prescribing physician via advance IT techniques about what pills have been disposed, which patient, etc. and the physician can then put this information into the appropriate patient's chart.
10. They will then be asked to pour the pills down the pill disposal intake port/chute where the pills will be counted by the pill counter. Liquid medication can also be dispensed into the kiosk via the liquid intake port/chute where the amount disposed will be measured and recorded.
11. The individual will be asked to complete steps 7, 8 & 10 until they have disposed of all of their medications.
12. When the individual has finished disposing all their medications into the kiosk, then he/she will be asked to verify the information shown on the touch/display screen. Listed on the screen will be the name(s) of the medication disposed, the number of pills disposed per medication, the reward/financial incentive amount and type the individual will be receiving, the name and number of controlled substances disposed, etc. The user will be reminded that the information concerning the disposal of the controlled substance will be relayed to the state's PDMP. The individual will have the option to print this information or have it sent to them electronically.
13. The individual will be asked to complete the medication disposal process and the payment of the incentive will be completed.
14. While the incentive payment is being generated, the individual will be reminded to dispose of their pill bottles in the TRxASH™ kiosk via the pill bottle disposal port/chute.
15. However, to avoid identity theft, they will be encouraged to remove the label from the pill bottle that contains their name and medication information, to take it home with them and to shred. However, if they cannot remove the label, they will be encouraged to use the identify theft stamps that are located on the TRxASH™ kiosk to blacken out their name and medication information before disposing of the pill bottles in the pill disposal chute,
16. Once the payment has been made, the individual will press finished and all information related to their visit to the kiosk will disappear from the touch/display screen. Their transaction will be completed. If the individual forgets to press finished, the kiosk will complete their transaction and their information will disappear from the touch/display screen as soon as the incentive payment has been made.
17. As another to keep plastic out of our land fields and to keep our planet beautiful and green, anyone will be allowed to dispose of empty pill bottles in the TRxASH™ kiosk at any time. They will be encouraged to remove prescription labels before disposing the pill bottles or to use the identity theft stamp located on the TRxASH™ kiosk to blacken out their name and medication information.
18. As a way to ensure that individuals can afford the medications they need and to help offset the increasing cost of medication, the individual will be able to use their reward/financial incentive to pay for new prescriptions or purchase other over-the-counter medication or anything else in the store/pharmacy they may need.

The procedure for dispensing medications into a Portable TRxASH™ kiosk at the any community health fair, by a community health worker, EMS, etc. or in any community setting is the same as above except disposal of the medications will be into the portal kiosk and the kiosk can have options for the coupon generated to be from any local pharmacy chain or hospital pharmacy or can be from a preset pharmacy based on previously established partnerships. Disposal will also be in accordance to the Drug Disposal Act.

The instant invention 10 is an AUTOMATED Medication Disposal and Reconciliation Kiosk that differs from any other medication disposal kiosks/systems because of the following benefits:

Is a safe, convenient, 24-hour a day, 7-days-a-week, year-round system that can PROVIDE A FINANCIAL INCENTIVE to get individuals to dispose of their unused or old medications so they can use the coupons to pay for new prescriptions, refills, food, store merchandise, etc., Can generate coupons as a financial incentive for individuals, thus encouraging the disposal of unused or old medications so they can use the coupons to pay for new prescriptions or refills (increasing medication compliance), food (decreasing food insecurities), store merchandise, etc., Can generate revenue for pharmacies and tail entities where they are housed, Can help to establish partnerships between pharmaceutical companies, pharmacies, health care providers and community entities, Can be used for medication reconciliation in both the outpatient provider's offices and on in-patient hospital medical and surgical floors prior to a patient's discharge from the provider's office and from the hospital, and communicate with the patient's electronic health record, Can be a way to dispose of recalled medications and generate information to the recalling pharmaceutical company in real-time, and Can capture and provide an extraordinary amount of data: Via Bluetooth capabilities, it can be programmed to record, generate, and provide information for prescribers, hospitals, pharmacies, local and state health departments, state PDMP systems, the CDC, DEA, etc. concerning medications that have been disposed, while exploring a possible correlation between the number of pills/controlled substances prescribed, disposed, and deaths due to overdoses, etc.

DOES NOT require the oversight of pharmacist or medical personnel,

Is a way to dispose of all prescription and over-the-counter medications, including controlled medications like opioids, etc.

Can STOP street selling of old controlled medications, such as opioids and benzos by giving individuals a financial incentive to dispose of them into the kiosk instead of selling them on the streets, thus making a big impact on addressing the Opioid Crisis and saving many lives.

Can decrease pre-hospital, hospital and overall health care cost by making medication in home medicine cabinets less accessible or available to be used for suicide attempts, drug overdosing, etc. and thus freeing up EMS for other emergency calls, hospital beds for other illnesses, rehab beds, etc.

Can STOP providers from sending the patient home with the tied-up plastic bag of "do not take" pills upon discharge from the provider's office, only to be placed in the family's medicine cabinet or pantry. But instead, allow for physicians or medical providers to perform medication reconciliation during each visit, with medications in hand, and then immediately dispose of discontinued or unused medications in the office, with the patient present, during the patient's visit.

Can STOP "family and friend sharing" of old medications and will stop individuals from keeping old, unused medications around the house to take at a later date or when they get ill again.

Can STOP the evolution of drug-resistant bacteria due to partially treated infections &/or the unnecessary use of antibiotics. This can occur when an individual gets sick, gets a few left-over antibiotics from a friend or family member for an illness that either did not require antibiotics or that did require antibiotics, but the wrong antibiotic was taken and so the bacterial infection was inadequately or partially treated due to the short course of treatment.

Can STOP the "teenage skittle game" by getting old and unused pills/medications out of family medicine cabinets.

Can STOP old or unused medication from being flushed down the toilet and ending up in local lakes, canals, oceans, etc. and preventing toxicity to fish, turtles, and other marine life.

Can use a non-toxic Bio-degradable solution or mixture that will immediately make pills unusable when they come in contact with it, Can vary in size and portability (small portable or larger stand-alone), so it can fit in numerous medical, non-medical, pharmacy and nonpharmacy convenient locations, Can allow for medication disposal to occur in various locations that people frequent and can include, but not be limited to:

Inpatient, outpatient and community pharmacies,
retail stores and grocery stores where a pharmacy is or is not located,
outpatient medical/dental/veterinary/specialist offices,
patient waiting rooms in doctor's offices,
EMS vehicles,
mobile health centers,
inpatient hospital medical and surgical floors, Emergency Departments
lobbies of senior center homes/condominiums, ALFs, Nursing Homes
community centers located in 55 and over communities, etc.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medication disposal, treatment and reconciliation device comprising:
    a housing;
    a microprocessor supported in said housing;
    a microprocessor readable code of instructions operable by said microprocessor;
    a video display monitor, in communication with said microprocessor and said microprocessor code of instructions, for displaying information derived from said microprocessor code of instructions;
    a user interface means, in communication with said microprocessor and said microprocessor readable code of instructions, for navigating said microprocessor code of instructions;
    a medication holding container;
    a medication deposit port in communication with said medication holding container;
    a medication measurement means, supported by said housing and in communication with said microprocessor readable code of instructions, for determining the amount of medication deposited into said medication holding container;
    a medication identification means, in communication with said medication holding container, for identification of medication deposited in said medication holding container; and
    compensation means, in communication with said microprocessor and said microprocessor readable code of instructions, for providing compensation incentives that may be redeemed for products or monetary considerations when medication is deposited in said medication holding container.

2. The device of claim 1, further comprising:
    a pill counter in communication with said microprocessor and said microprocessor readable code of instructions.

3. The device of claim 1, further comprising:
an electronic scale in communication with said microprocessor and said microprocessor readable code of instructions for weighing medication.

4. The device of claim 1, further comprising:
a wireless communication means, in communication with said microprocessor and said microprocessor readable code of instructions, for communicating and transmitting data to predetermined agencies, such as PDMP's, PCP's, medical offices, and other predetermined third parties.

5. The device of claim 1, further comprising:
a contactless mobile communication device reader in communication with said microprocessor and said microprocessor readable code of instructions.

6. The device of claim 1, further comprising:
an advertisement display screen in communication with said microprocessor and said microprocessor readable code of instructions.

7. The device of claim 1, further comprising:
a barcode reader in communication with said microprocessor and said microprocessor readable code of instructions.

8. The device of claim 1, further comprising:
a scanner in communication with said microprocessor and said microprocessor readable code of instructions.

9. The device of claim 1, further comprising:
an e-coupon transmitter in communication with said microprocessor and said microprocessor readable code of instructions.

10. The device of claim 1, further comprising:
a printer in communication with said microprocessor and said microprocessor readable code of instructions.

11. The device of claim 1, further comprising:
a mobile app operable by a mobile communication device for communicating with said microprocessor and said microprocessor readable code of instructions.

12. The device of claim 1, further comprising:
a reward card reader in communication with said microprocessor and said microprocessor readable code of instructions.

13. The device of claim 1, further comprising:
an identification reader in communication with said microprocessor and said microprocessor readable code of instructions.

14. The device of claim 1, further comprising:
a receipt generator in communication with said microprocessor and said microprocessor readable code of instructions.

15. The device of claim 1, further comprising:
a coupon generator in communication with said microprocessor and said microprocessor readable code of instructions.

16. The device of claim 1, wherein said monitor comprises a touchscreen.

17. The device of claim 1, wherein said microprocessor readable code of instructions comprises:
login means for accessing and operating said code of instructions;
identification means for identifying the user of said device'
medication disposal selection and authorization means for enabling the disposal of medication;
medication reconciliation means for identifying the type and amount of the medication disposed; and
reward generation means for generating compensation for disposal of the medication.

18. The device of claim 17, wherein said code of instructions further comprises:
information transmission means for sending medication data to a predetermined entity or location.

19. The device of claim 17, wherein said code of instructions further comprises:
compensation selection means for enabling a user to choose said compensation.

20. The device of claim 17, further comprising:
a sensor indicator for indicating the relevant amount of medication in said medication container.

* * * * *